United States Patent
Lee et al.

(10) Patent No.: US 11,642,086 B2
(45) Date of Patent: May 9, 2023

(54) APPARATUS AND METHOD FOR CORRECTING ERROR OF BIO-INFORMATION SENSOR, AND APPARATUS AND METHOD FOR ESTIMATING BIO-INFORMATION

(71) Applicant: SAMSUNG ELECTRONICS CO., LTD., Suwon-si (KR)

(72) Inventors: So Young Lee, Daejeon (KR); Jin Young Park, Hwaseong-si (KR); Ka Ram Ram Choi, Seoul (KR); Sang Kon Bae, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 85 days.

(21) Appl. No.: 17/329,706

(22) Filed: May 25, 2021

(65) Prior Publication Data

US 2021/0275104 A1 Sep. 9, 2021

Related U.S. Application Data

(62) Division of application No. 16/002,647, filed on Jun. 7, 2018, now Pat. No. 11,058,358.

(30) Foreign Application Priority Data

Oct. 17, 2017 (KR) .................. 10-2017-0134841

(51) Int. Cl.
*A61B 5/00* (2006.01)
*A61B 5/0205* (2006.01)
(Continued)

(52) U.S. Cl.
CPC ........ *A61B 5/7203* (2013.01); *A61B 5/02055* (2013.01); *A61B 5/14532* (2013.01);
(Continued)

(58) Field of Classification Search
CPC .............. A61B 5/7203; A61B 5/02055; A61B 5/14532; A61B 5/4866; A61B 5/7221;
(Continued)

(56) References Cited

U.S. PATENT DOCUMENTS

| 5,840,020 A | 11/1998 | Heinonen et al. |
| 6,269,314 B1 | 7/2001 | Titawaki et al. |

(Continued)

FOREIGN PATENT DOCUMENTS

| CN | 105653865 A | 6/2016 |
| JP | 11-56822 A | 3/1999 |

(Continued)

OTHER PUBLICATIONS

Staal, et al., "Kalman Smoothing of Glucose Data: Applied to Partial Least Squares Modeling of Non-Invasive Near-Infrared Measurements", 2017, Prediktor: ATTD Conference, POSTER, 1 page total.

(Continued)

*Primary Examiner* — Catherine M Voorhees
*Assistant Examiner* — Roland Dinga
(74) *Attorney, Agent, or Firm* — Sughrue Mion, PLLC

(57) ABSTRACT

An apparatus for providing corrected bio-information by using a bio-information sensor includes a communicator configured to receive bio-information from the bio-information sensor; a processor configured to extract metabolic information based on food intake information of a user and correct the received bio-information based on the extracted metabolic information; and an outputter configured to provide a result of correcting the bio-information.

14 Claims, 16 Drawing Sheets

(51) Int. Cl.
    *A61B 5/145*     (2006.01)
    *G16H 50/20*     (2018.01)
    *G16H 20/60*     (2018.01)
    *A61B 8/00*     (2006.01)
    *A61B 5/01*     (2006.01)
    *A61B 5/024*     (2006.01)
    *A61B 5/053*     (2021.01)
    *A61B 5/318*     (2021.01)
    *A61B 5/369*     (2021.01)
    *A61B 5/389*     (2021.01)
    *A61B 5/398*     (2021.01)

(52) U.S. Cl.
    CPC .......... *A61B 5/4866* (2013.01); *A61B 5/7221* (2013.01); *A61B 5/7246* (2013.01); *A61B 5/7275* (2013.01); *A61B 5/7278* (2013.01); *G16H 20/60* (2018.01); *G16H 50/20* (2018.01); *A61B 5/0075* (2013.01); *A61B 5/01* (2013.01); *A61B 5/0205* (2013.01); *A61B 5/02416* (2013.01); *A61B 5/053* (2013.01); *A61B 5/14546* (2013.01); *A61B 5/318* (2021.01); *A61B 5/369* (2021.01); *A61B 5/389* (2021.01); *A61B 5/398* (2021.01); *A61B 5/4845* (2013.01); *A61B 5/681* (2013.01); *A61B 8/00* (2013.01)

(58) Field of Classification Search
    CPC ... A61B 5/7246; A61B 5/7275; A61B 5/7278; A61B 5/398; A61B 5/369; A61B 5/318; A61B 5/389; A61B 5/0075; A61B 5/01; A61B 5/0205; A61B 5/02416; A61B 5/053; A61B 5/14546; A61B 5/4845; A61B 5/681; A61B 8/00
    See application file for complete search history.

(56) References Cited

U.S. PATENT DOCUMENTS

| | | |
|---|---|---|
| 6,569,094 B2 | 5/2003 | Suzuki et al. |
| 6,985,078 B2 | 1/2006 | Ssuki et al. |
| 7,840,269 B2 | 11/2010 | Policker et al. |
| 7,878,975 B2 | 2/2011 | Liljeryd et al. |
| 8,858,435 B2 | 10/2014 | Liljeryd et al. |
| 9,384,324 B2 | 7/2016 | Liljeryd et al. |
| 9,439,602 B2 | 9/2016 | Sparacino et al. |
| 2004/0142402 A1 | 7/2004 | Maruo et al. |
| 2005/0096637 A1 | 5/2005 | Heruth |
| 2006/0167348 A1 | 7/2006 | Arnold et al. |
| 2007/0288216 A1 | 12/2007 | Kouchi et al. |
| 2010/0249530 A1 | 9/2010 | Rankers et al. |
| 2011/0098548 A1 | 4/2011 | Budiman et al. |
| 2011/0118987 A1 | 5/2011 | Takeuchi et al. |
| 2012/0259389 A1 | 10/2012 | Starkebaum et al. |
| 2014/0012510 A1 | 1/2014 | Mensinger et al. |
| 2014/0188402 A1 | 7/2014 | Garica et al. |
| 2016/0012749 A1 | 1/2016 | Connor |
| 2016/0213290 A1 | 7/2016 | Park et al. |
| 2016/0345842 A1 | 12/2016 | Liljeryd et al. |
| 2017/0242975 A1* | 8/2017 | Kahlbaugh ............ G16H 20/40 |
| 2018/0020956 A1* | 1/2018 | Lee ........................ G01N 21/65 600/306 |
| 2018/0146899 A1* | 5/2018 | Lee ..................... A61M 5/1723 |

FOREIGN PATENT DOCUMENTS

| | | |
|---|---|---|
| JP | 2000-503556 A | 3/2000 |
| JP | 2001-327472 A | 11/2001 |
| JP | 2007-523709 A | 8/2007 |
| JP | 4853207 B2 | 1/2012 |
| JP | 2012-24476 A | 2/2012 |
| JP | 2014-147404 A | 8/2014 |
| JP | 5648355 B2 | 1/2015 |
| JP | 6108930 B2 | 4/2017 |
| KR | 10-2016-0007678 A | 1/2016 |
| KR | 10-2017-0055409 A | 5/2017 |

OTHER PUBLICATIONS

Sadikoglu, et al., "Filtering continuous glucose monitoring signal using Savitzky-Golay filter and Simple Multivariate Thresholding", Aug. 2016, Procedia Computer Science, vol. 102, pp. 342-350.

Search Report dated Mar. 1, 2019 by the European patent Office in counterpart European Patent Application No. 18184919.1.

Staal, et al., "Kalman Smoothing for Objective and Automatic Preprocessing of Glucose Data", 2018, IEEE Journal of BioMedical and Health Informatics, 9 pages total.

Communication dated Jan. 25, 2022 by the Japanese Patent Office in counterpart Japanese Patent English Application No. 2018-155762 translation.

* cited by examiner (1) $dC_1 = -(K_{10} + K_{12})C_1 + K_{21}C_2$
(2) $dC_2 = K_{12}C_1 - K_{21}C_2$

APPARATUS AND METHOD FOR CORRECTING ERROR OF BIO-INFORMATION SENSOR, AND APPARATUS AND METHOD FOR ESTIMATING BIO-INFORMATION

CROSS-REFERENCE TO RELATED APPLICATION(S)

This is a divisional application of U.S. application Ser. No. 16/002,647, filed Jun. 7, 2018, which claims priority from Korean Patent Application No. 10-2017-0134841, filed on Oct. 17, 2017, in the Korean Intellectual Property Office, the entire disclosure of which is incorporated herein by reference in its entirety.

BACKGROUND

1. Field

Apparatuses and methods consistent with exemplary embodiments relate to correcting a measurement error of a bio-information measurement sensor and non-invasively estimating bio-information.

2. Description of Related Art

Diabetes is a chronic disease that causes various complications and can be hardly cured, and hence blood glucose should be regularly monitored to prevent complications. In addition, when insulin is administered, it is necessary to check blood glucose in an effort to avoid hypoglycemia and control insulin dosage. Generally, an invasive method is used to measure blood glucose. The method of invasively measuring blood glucose may provide high reliability in measurement, but it causes pain from blood sampling, inconvenience and a risk of disease infection due to the use of injection. Recently, methods of non-invasively estimating a biological component, such as blood glucose, through spectrum analysis by use of a spectrometer, without directly collecting blood, have been studied.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided an apparatus of providing corrected bio-information by using a bio-information sensor, the apparatus including: a communicator configured to receive bio-information from the bio-information sensor; a processor configured to extract metabolic information based on food intake information of a user and correct the received bio-information based on the extracted metabolic information; and an outputter configured to provide a result of correcting the bio-information.

The processor may acquire the food intake information based on at least one from among food intake sensor information received from a food intake sensor and information input by the user.

The processor may obtain a slope change of the bio-information based on continuous bio-information measurements included in the bio-information received from the bio-information sensor and acquire the food intake information based on the slope change.

The food intake information may include at least one from among a type of food taken, an amount of the food taken, and a food intake time.

The metabolic information may include at least one from among a change amount of the bio-information over time, a confidence interval of the bio-information, and a probability of the change amount being in a certain variation range.

The processor may extract the metabolic information by using at least one from among a physiological metabolic model and a bio-information database.

The processor may correct a measurement of the received bio-information by using at least one from among a correction formula and a correlation model of the measurement and the metabolic information.

The processor may determine that a measurement of the received bio-information which is out of a confidence interval of the bio-information as an outlier value, and correct the determined outlier value to a value within the confidence interval.

The processor may correct a measurement of the received bio-information that is determined as not being based on an actual measurement of the bio-information, correcting the measurement being based on at least one from among a change amount of the bio-information over time and a probability of the change amount being in a certain variation range.

The bio-information may include at least one from among blood glucose, cholesterol, triglycerides, protein, alcohol, and uric acid.

According to another aspect of an exemplary embodiment, there is provided a method of providing corrected bio-information by using a bio-information sensor, the method including: receiving bio-information from the bio-information sensor; extracting metabolic information based on food intake information of a user; and correcting the received bio-information based on the extracted metabolic information and providing a result of correcting the bio-information.

The method may further include receiving food intake sensor information from a food intake sensor; and acquiring the food intake information based on the received food intake sensor information.

The method may further include obtaining a slope change of the bio-information based on continuous measurements included in the received bio-information; and acquiring the food intake information based on the slope change.

The metabolic information may include at least one from among a change amount of the bio-information over time, a confidence interval of the bio-information, and a probability of the change amount being in a certain variation range.

The extracting the metabolic information may include extracting the metabolic information by using at least one from among a physiological metabolic model and a bio-information database.

The correcting the bio-information may include at least one from among correcting an outlier value which is out of a confidence interval of the bio-information and correcting a measurement of the received bio-information that is determined as not being based on an actual measurement of the bio-information.

According to still another aspect of an exemplary embodiment, there is provided an apparatus for estimating bio-information, including: a sensor configured to obtain sensor information from a user; and a processor configured to estimate the bio-information based on the sensor information, extract metabolic information based on food intake information of the user, correct the estimated bio-information using the extracted metabolic information, and provide a result of correcting the estimated bio-information.

The sensor information may include at least one from among spectrometer measurement information, impedance measurement information, ultrasonic measurement information, thermal measurement information, electrocardiography (ECG) information, electroencephalogram (EEG) information, electromyography (EMG) information, electrooculography (EOG) information, and photoplethysmography (PPG) information.

The sensor may include a food intake sensor configured to acquire food intake sensor information by detecting a food intake of the user, and the processor is further configured to acquire the food intake information based on the food intake sensor information.

The processor may extract the metabolic information by using at least one from among a physiological metabolic model and a bio-information database.

The metabolic information may include at least one from among a change amount of the bio-information over time, a confidence interval of the bio-information, and a probability of the change amount being in a certain variation range.

The processor may correct an estimate of the bio-information by using at least one from among a correlation model and a correction formula indicating a correlation between the estimate of the bio-information and the change amount of the bio-information over time or the probability of the change amount being in the certain variation range.

The processor may correct an outlier value among estimates of the bio-information which is out of the confidence interval with a value within the confidence interval.

The processor may determine an estimate of the bio-information as not being based on an actual measurement of the bio-information and correct the estimate based on at least one from among the change amount of the bio-information over time and the probability of the change amount of the bio-information being in the certain variation range.

According to still another aspect of an exemplary embodiment, there is provided a method of estimating bio-information, including: obtaining sensor information from a user; estimating bio-information based on the sensor information; acquiring food intake information of the user; extracting metabolic information based on the food intake information; and correcting the estimated bio-information based on the extracted metabolic information and providing a result of correcting the estimated bio-information.

The sensor information may include at least one from among spectrometer measurement information, impedance measurement information, ultrasonic measurement information, thermal measurement information, ECG information, EEG information, EMG information, EOG information, and PPG information.

The obtaining the sensor information may include obtaining food intake sensor information by using a food intake sensor configured to detect a food intake of the user and the acquiring the food intake information includes acquiring the food intake information of the user based on the food intake sensor information.

The extracting the metabolic information may include extracting the metabolic information by using at least one from among a physiological metabolic model and a bio-information database.

The correcting the bio-information may include at least one from among correcting an outlier value which is out of a confidence interval of the bio-information and correcting an estimate of the received bio-information that is determined as not being based on an actual measurement of the bio-information.

BRIEF DESCRIPTION OF THE DRAWINGS

The above and/or other aspects of the disclosure will become apparent and more readily appreciated from the following description of the exemplary embodiments, taken in conjunction with the accompanying drawings.

DETAILED DESCRIPTION

Figure 1:
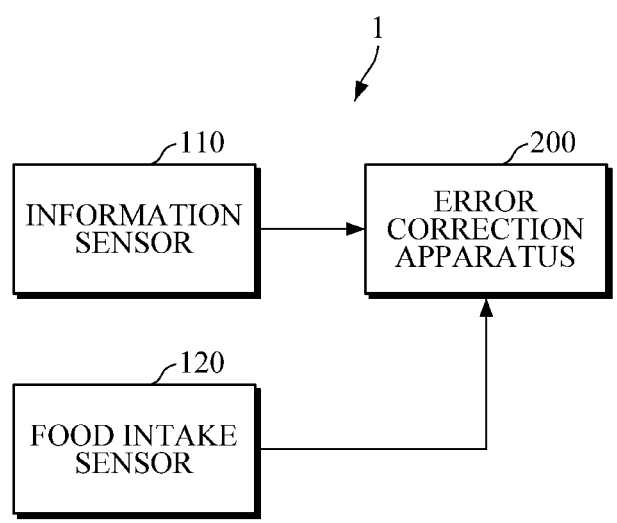
FIG. 1 is a block diagram illustrating a bio-information measurement system according to an exemplary embodiment.

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

Hereinafter, exemplary embodiments will be described in detail with reference to the drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising", will be understood to imply the inclusion of stated elements but not the exclusion of any other elements. Terms such as " . . . unit" and "module" denote units that process at least one function or operation, and they may be implemented by using hardware, software, or a combination of hardware and software.

FIG. 1 is a block diagram illustrating a bio-information measurement system according to an exemplary embodiment.

Referring to FIG. 1, a bio-information measurement system 1 includes a bio-information sensor 110, a food intake sensor 120, and an error correction apparatus 200.

The bio-information sensor 110 measures bio-information from a user. The bio-information sensor 110 may be attached to or worn on a part to be inspected to measure the bio-information from the corresponding part. The bio-information sensor 110 may include a sensor configured to continuously measure bio-information at predetermined time intervals (e.g., 5 minutes, 10 minutes, 15 minutes, etc.), for example, a continuous blood glucose measurement sensor. In this case, the bio-information sensor 110 may be a non-invasive sensor that measures the bio-information based on sensor information obtained from various sensors, for example, spectrometer measurement information, such as spectral information, impedance measurement information, ultrasonic measurement information, thermal measurement information, electrocardiography (ECG) information, electroencephalogram (EEG) information, electromyography (EMG) information, electrooculography (EOG) information, and photoplethysmography (PPG) information. However, the type of sensor is not limited to the above examples. For example, the bio-information sensor may include an invasive or minimally invasive sensor. The bio-information may include, but is not limited to, one or more of blood glucose, cholesterol, triglycerides, protein, alcohol, and uric acid.

The food intake sensor 120 may detect the user's food intake and generate food intake sensor information. The food intake sensor 120 may be provided as a separate hardware device to be attached to or worn on a body part of the user. Alternatively, the food intake sensor 120 may be mounted in the bio-information sensor 110 or the error correction apparatus 200. For example, the food intake sensor 120 may include a sensor that is worn on a user's ear and detects the user's food intake sounds, a gyro sensor that is worn on a user's wrist and detects a user's arm motion, a sensor that detects a user's chest movement or respiratory, a sensor that senses food that the user is eating, a piezoelectric sensor that detects the user's swallowing or muscle movement of a neck, and the like. Alternatively, the food intake sensor 120 may include a camera module and the like which acquires image information related to the user's food intake.

The error correction apparatus 200 may receive continuous bio-information measurements from the bio-information sensor 110. When the error correction apparatus 200 receives the bio-information from the bio-information sensor 110, the error correction apparatus 200 may correct the bio-information based on the user's food intake information and output the correction result as final bio-information. In this case, the food intake information may include one or more of an intake food, a food intake amount, and a food intake time.

Figure 2:
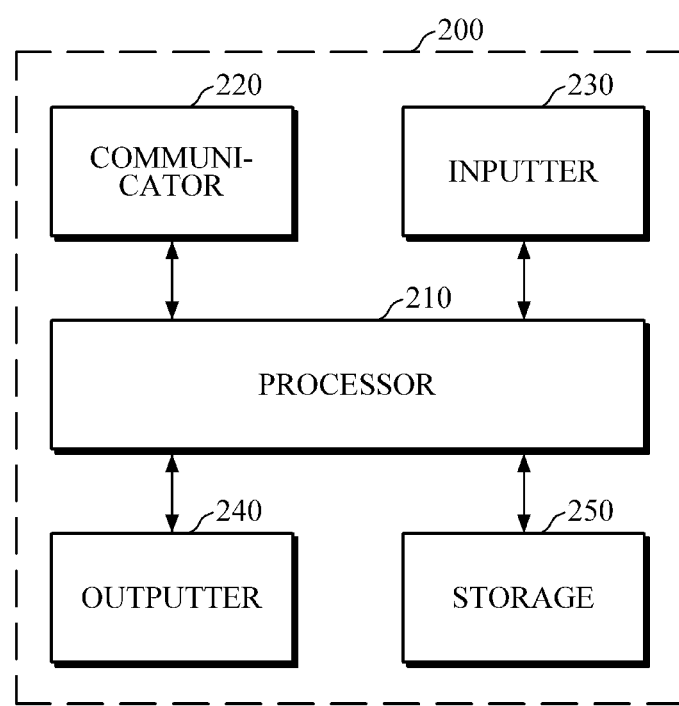
FIG. 2 is a block diagram illustrating an apparatus of correcting an error of a bio-information sensor according to an exemplary embodiment.
Figure 3:
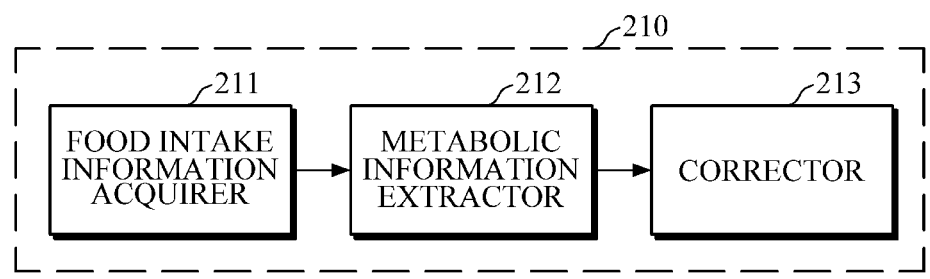
FIG. 3 is a block diagram illustrating a configuration of a processor according to an exemplary embodiment of FIG. 2.
Figure 4:
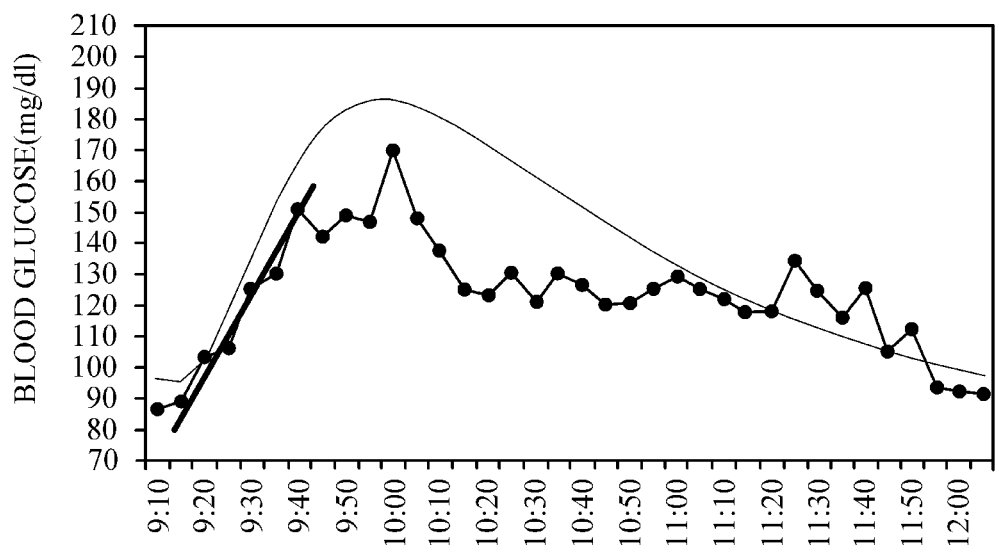
FIG. 4 is a diagram for describing an exemplary embodiment of acquiring intake information.

FIG. 2 is a block diagram illustrating an apparatus of correcting an error of a bio-information sensor according to an exemplary embodiment. FIG. 3 is a block diagram illustrating a configuration of a processor according to an exemplary embodiment of FIG. 2. FIG. 4 is a diagram for describing an exemplary embodiment of acquiring intake information.

The error correction apparatus 200 according to an exemplary embodiment may be a hardware device physically independent of (or separate from) the bio-information sensor 110. For example, the error correction apparatus 200 which is an information processing device, such as a smartphone, a tablet personal computer (PC), a notebook PC, a desktop PC, and a server, is not particularly limited in terms of portability and size, and may be provided in various forms according to the application purpose of the error correction apparatus 200.

Referring to FIG. 2, the error correction apparatus 200 includes a processor 210, a communicator 220, an inputter 230, an outputter 240, and a storage 250.

The communicator 220 may communicate with an external device, including the bio-information sensor 110, by using a communication technology under the control of the processor 210, and may transmit and receive various items of data. For example, the communicator 220 may receive a bio-information measurement from the bio-information sensor 110 at a predetermined time interval and transmit the received measurement to the processor 210, and also may transmit a processing result of the processor 210 to the external device. In this case, the external device may be a user's device providing excellent computing performance, such as a smartphone, a tablet PC, a desktop PC, or a notebook PC, or a computing medical device in a medical institution.

The communication technology may include a Bluetooth communication, a Bluetooth low energy communication, a near-field communication (NFC), a wireless local area network (WLAN) communication, a ultra-wideband (UWB) communication, an Ant+ communication, a Wi-Fi communication, and a mobile communication, but is not limited thereto.

In addition, the communicator 220 may communicate with the food intake sensor 120 under the control of the processor 210, receive the food intake sensor information and transmit the received information to the processor 210.

The inputter 230 may receive a variety of information including the food intake information from the user and transmit the information to the processor 210. The inputter 230 may output a user interface to a display and receive a variety of information input by the user through the user interface. Alternatively, when the error correction apparatus 200 employs a voice recognition technology, the inputter 230 may receive voice information input by the user. However, exemplary embodiments are not limited thereto, and the inputter 230 may be variously embodied in accordance with user input methods. For example, the inputter 230 may include a keyboard, a virtual keyboard on a touch screen, a remote control signal receiver for receiving a remote control signal corresponding to a user input from a remote controller, a camera for sensing a user gesture input, a microphone for receiving a user's voice input, etc.

The processor 210 may receive the bio-information from the bio-information sensor 110 through the communicator 220 and correct the bio-information based on the food intake information.

Referring to FIG. 3, the processor 210 includes a food intake information acquirer 211, a metabolic information extractor 212, and a corrector 213.

The food intake information acquirer 211 may acquire food intake information by analyzing the food intake sensor information received from the food intake sensor 120 or continuous bio-information measurements received from the bio-information sensor 110. Alternatively, the food intake information acquirer 211 may acquire food intake information directly input by the user through an interface.

For example, when the food intake information acquirer 211 receives the food intake sensor information, such as a food intake sound, a captured food image, information of swallowing detection, information of arm movement detection, or the like, the food intake information acquirer 211 may analyze the received food intake sensor information to acquire food intake information, such as a type and an amount of food taken by the user, or the food intake time.

In another example, the food intake information acquirer 211 may obtain a slope change of the bio-information by analyzing the continuous bio-information measurements received from the bio-information sensor 110 and, and acquire the food intake information based on the slope change. FIG. 4 is a graph showing an exemplary embodiment of continuous blood glucose measurements received from a blood glucose measurement sensor. In FIG. 4, an abrupt slope change of the blood glucose level is shown from around 9:10 to around 9:40. The food intake information acquirer 211 may determine that a point in time at which the slope change of the blood glucose level is drastic is when the user took the food. In addition, the food intake information acquirer 211 may estimate the type or amount of food that the user has eaten based on information predefined for the user indicating a correlation between a change in blood glucose level and food information.

The metabolic information extractor 212 may extract metabolic information based on the food intake information. In this case, the metabolic information may include a change amount of bio-information with respect to time, a confidence interval of the bio-information, and a probability or frequency of each variation range of the bio-information.

FIGS. 5A to 5D are diagrams for describing exemplary embodiments of extracting metabolic information. An exemplary embodiment in which the metabolic information extractor 212 extracts metabolic information will be described with reference to FIG. 2 and FIGS. 5A to 5D.

For example, when the food intake information of the user is acquired, the metabolic information extractor 212 may extract a change amount of bio-information with respect to time using a physiological metabolic model according to a transfer of a substance related to the bio-information among organs in a human body.

Figure 5A:
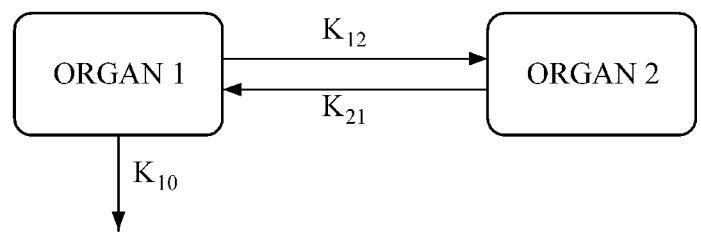
FIGS. 5A to 5D are diagrams for describing exemplary embodiments of extracting metabolic information.

FIG. 5A illustrates an example of a metabolic model in which blood glucose metabolism according to the substance transfer between organ 1 (e.g., stomach) and organ 2 (e.g., intestine) in the human body is mathematized. In the example metabolic model shown in FIG. 5A, $K_{10}$ represents a substance transfer constant when the substance is discharged from organ 1, $K_{12}$ represents a substance transfer constant when the substance is transferred from organ 1 to organ 2, and $K_{21}$ represents a substance transfer constant when the substance is transferred from organ 2 to organ 1. $C_1$ and $C_2$ represent blood glucose concentrations in organ 1 and organ 2, respectively, and $dC_1$ and $dC_2$ represent variations in blood glucose level in organ 1 and organ 2, respectively. The physiological metabolic model may be personalized by modeling various factors of individual users related to internal absorption or distribution of substances, metabolism of organs, such as a liver and a stomach, exertion, and the like.

Figure 5B:
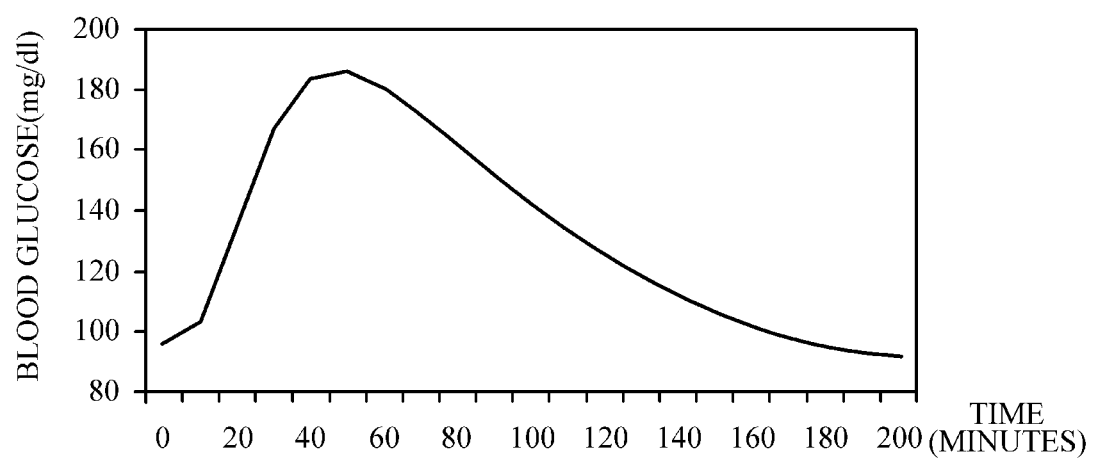

FIG. 5B is an example of estimating a change amount over time of blood glucose level which is estimated using a physiological metabolic model when user's food intake information is given, for example, when the user takes 75 grams of sugar.

Figure 5C:
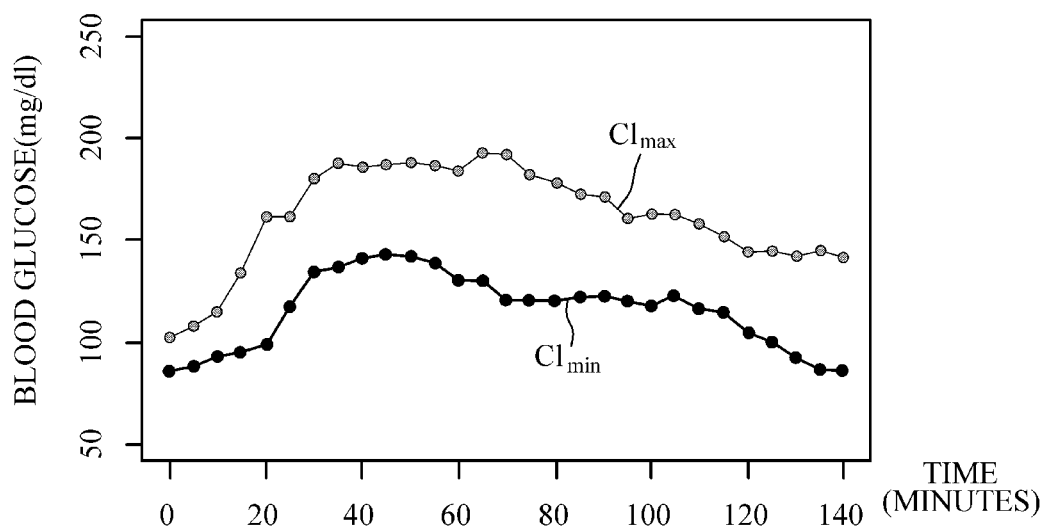
Figure 5D:
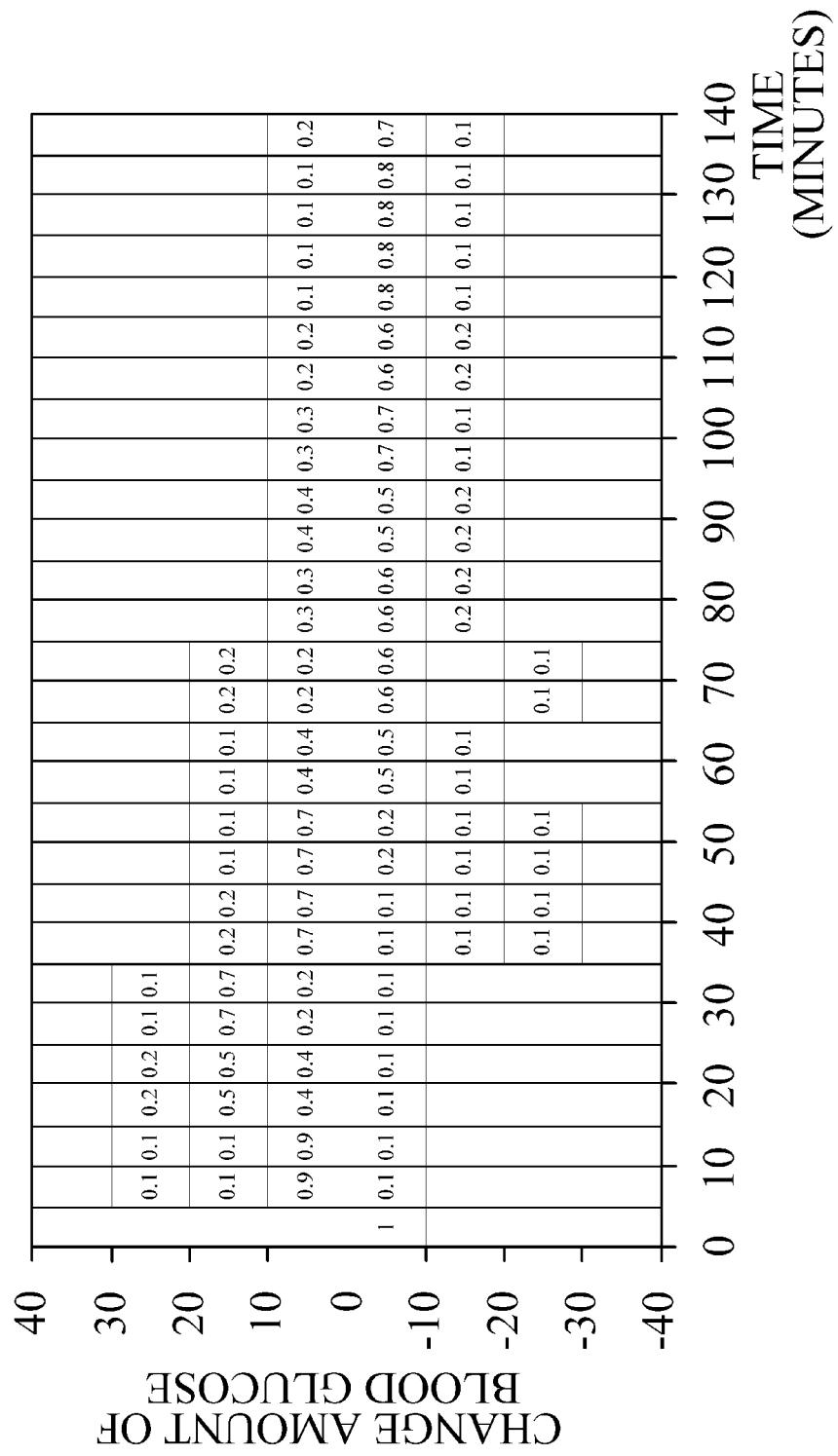

In another example, the metabolic information extractor 212 may extract a confidence interval of the bio-information, or probability or frequency information of a variation range of the bio-information according to time with respect to the food intake information by referring to a bio-information database established in advance. The bio-information database may include time-based bio-information measurements according to the type or amount of food eaten related to the bio-information for each user. Referring to FIG. 5C, the metabolic information extractor 212 may extract a confidence interval according to time, for example, a minimum value $CI_{min}$ and a maximum value $CI_{max}$. FIG. 5D shows a probability of a change amount over time of a blood glucose level being in each variation range, which is extracted by the metabolic information extractor 212 by referring to the bio-information database.

When the metabolic information extractor 212 extracts the information, such as a change amount over time of bio-information, the confidence interval, or a probability of each variation range, the corrector 213 may correct the measurement values, outlier values or missing values of bio-information received from the bio-information sensor 110 using the metabolic information.

FIGS. 6A to 6D are graphs for describing exemplary embodiments of correcting an error of bio-information. Exemplary embodiments in which the corrector 213 corrects the bio-information received from the bio-information sensor 110 will be described with reference to FIGS. 6A to 6D.

In one example, the corrector 213 may correct the bio-information measurement measured by the bio-information sensor 110 using a correction formula of the bio-information or a correlation model. The correlation model may be provided in advance through linear regression modeling or machine learning modeling a relationship among the bio-information measurement obtained by the bio-information sensor, a change amount over time of bio-information in the metabolic information, and an actual bio-information measurement obtained through blood collection. In addition, the correction formula of the bio-information may be a linear function predefined as shown in Equation 1 or Equation 2 below. However, Equation 1 and Equation 2 are merely examples and exemplary embodiments are not limited thereto.

$$G_t = w_1 M_t + w_2 N_t \tag{1}$$

$$G_t = N_t - w_1 M_t \tag{2}$$

Equation 1 is an example in which correction is performed by applying a weight to the bio-information measurement $N_t$ and a bio-information variation $M_t$ at a specific time point t and summing the weighted values. Equation 2 is an example in which correction is performed by subtracting a weighted bio-information variation $M_t$ from the bio-information measurement $N_t$ at a specific time point t. Here, $w_1$ and $w_2$ represent weights applied to the bio-information measurement $N_t$ and the bio-information variation $M_t$, respectively, at a specific time point t, and $G_t$ represents a correction result at the specific time point t.

Figure 6A:
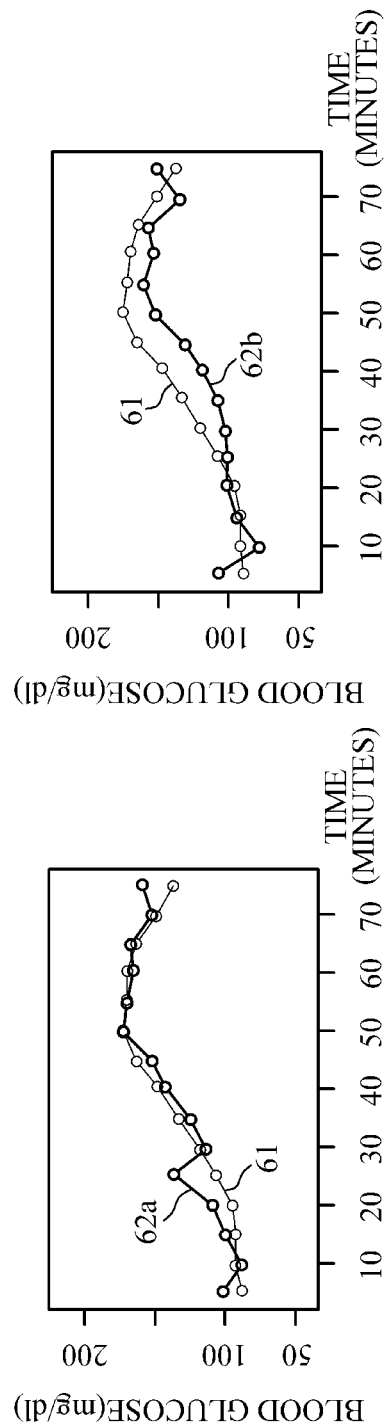
FIGS. 6A to 6D are graphs for describing exemplary embodiments of correcting an error of bio-information.

FIG. 6A shows a result of comparing actual blood glucose measurements 61 obtained through blood collection with a correction result 62a obtained by correcting the blood glucose measurements measured by a blood glucose sensor using the above Equation 1, and a result of comparing the actual blood glucose measurements 61 with blood measurements 62b corrected using a related art smoothing method. As shown in the graphs of FIG. 6A, it can be seen that the correction result 62a of the blood glucose measurements according to an exemplary embodiment is more similar to the actual blood glucose measurements 61 obtained through blood collection than the blood glucose measurements 62b obtained by the related art smoothing method.

In another example, the corrector 213 may correct an outlier value among the bio-information measurements measured by the bio-information sensor 110. The corrector 213 may determine an outlier value among the bio-information measurements based on confidence interval information of the bio-information extracted by the metabolic information extractor 211. For example, when a bio-information measurement at a specific point in time is out of the confident interval shown in FIG. 5C, for example, when the bio-information measurement is less than the minimum value $CI_{min}$ or greater than the maximum value $CI_{max}$ at the same point in time, the corrector 213 may determine that the bio-information measurement value is an outlier value.

When the bio-information measurement at the specific point in time is determined as an outlier value, the corrector 213 may correct the determined outlier value by replacing the outlier value with an arbitrary value within the confidence interval at the same point in time. For example, the corrector 213 may replace the outlier value with a boundary value of the confidence interval at the same point in time. In other words, when the outlier value is less than the minimum value $CI_{min}$ of the confidence interval, the outlier value may be replaced with the minimum value $CI_{min}$, and when the outlier value is greater than the maximum value $CI_{max}$ of the confidence interval, the outlier value may be replaced with the maximum value $CI_{max}$. Alternatively, the corrector 213 may correct the outlier value by subtracting a weighted bio-information variation from the outlier value, as shown in the above Equation 2, such that the outlier value becomes a value within the confidence interval. When the outlier value of the bio-information is corrected, the corrector 213 may smooth the corrected bio-information.

Figure 6B:
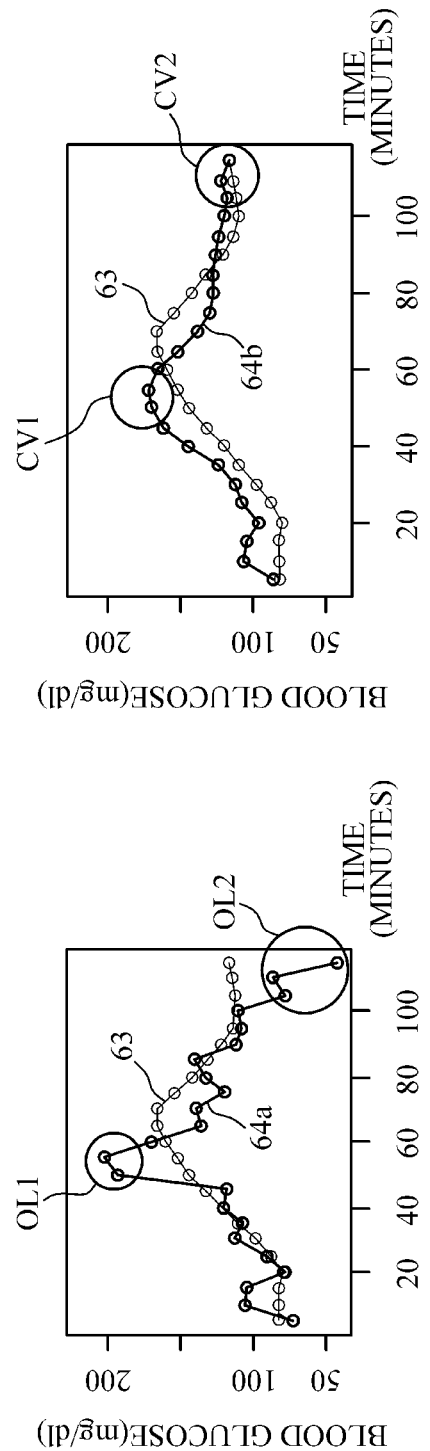

FIG. 6B illustrates graphs showing a result of comparing actual blood glucose measurements 63 obtained through blood collection with blood glucose measurements 64a received from the bio-information sensor 110 and a result of comparing the actual blood glucose measurements 63 with measurements 64b after correcting outlier values. Outlier values OL1 and OL2 that are out of a confidence interval are present in the blood glucose measurements 64a received from the bio-information sensor 110. By correcting the outlier values OL1 and OL2 that are out of the confidence interval to be boundary values CV1 and CV2 of the confidence interval, the outlier values may become similar to the actual blood glucose measurements 63.

In another example, the corrector 213 may correct a missing value of the bio-information measured by the bio-information sensor 110. Here, correcting the missing value may mean replacing a point in time or a time interval of the received measurements with a corrected value(s) when it is determined that the bio-information measurement is not actually performed at the point in time or in the time interval. For example, the corrector 213 may analyze the measurements received from the bio-information sensor 110 and estimate a missing value of the bio-information measurement. Here, estimating the missing value may mean determining a missing interval or a point in time where the actual bio-information measurement is not performed, based on a result of analyzing the bio-information measurements. For example, the missing value may be estimated based on continuous bio-information measurements received from the bio-information sensor 110. The missing value may occur in various situations such as, for example, when the user does not wear the bio-information sensor 110 for a certain period of time, when the power is turned off, or when the bio-information sensor 110 is in poor contact with the user's body part to be inspected.

When the missing value is estimated, the corrector 213 may correct the missing value using the bio-information variation or the probability information of each variation range extracted by the extractor 212. For example, the corrector 213 may correct a missing value $N_t$ at a specific time point t using a bio-information variation $M_t$ at the same time point t through Equation 3 below. However, Equation 3 is merely an example, and the missing value $N_t$ may be corrected by using various methods, such as, for example, replacing the missing value $N_t$ with the bio-information variation $M_t$ at the same time point t, replacing the missing value $N_t$ with an average or an intermediate value of bio-information variations $(M_{t-1}, M_{t+1})$ at the preceding and subsequent time points (e.g., t−1 and t+1) of the specific time point t, and the like.

$$G_t = N_1 + (M_t - M_1) \quad (3)$$

Here, $N_1$ represents a bio-information measurement at an initial time point (t=1), and $M_1$ represents a bio-information variation at the initial time point (t=1). In addition, $G_t$ represents a result of correcting a missing value at a specific time point t.

In addition, the corrector 213 may correct the missing value based on Table 1 below. Table 1 shows counts of range transitions according to a predetermined time before a missing time point t based on bio-information probability information for each variation range of FIG. 5. In Table 1, $G_{t-3}$, $G_{t-2}$, $G_{t-1}$, and $G_t$ represent bio-information measurements or corrected values at time points t−3, t−2, t−1, and t, respectively. For example, when a bio-information measurement $N_{t-3}$ is present at a specific time point t−3 and is not an outlier value, $G_{t-3}$ may be the bio-information measurement $N_{t-3}$ or a corrected value obtained by the above Equation 1 or 2. When the bio-information measurement $N_{t-3}$ is an outlier value or a missing value, $G_{t-3}$ may be a corrected value obtained by correcting the outlier value or the missing value as described above.

TABLE 1

| $G_{t-2}$-$G_{t-3}$ | $G_{t-1}$-$G_{t-2}$ | $G_{t-1}$-$G_t$ | Count |
|---|---|---|---|
| 0~+10 | 0~+10 | −30~−20 | 1 |
| 0~+10 | 0~+10 | −20~−10 | 5 |
| 0~+10 | 0~+10 | −10~0 | 22 |
| 0~+10 | 0~+10 | 0~+10 | 67 |
| 0~+10 | 0~+10 | +10~+20 | 18 |
| 0~+10 | 0~+10 | +20~+30 | 2 |

Referring to Table 1, when bio-information transition from $G_{t-2}$ to $G_{t-3}$ in a first interval (t−3 to t−2) and bio-information transition from $G_{t-1}$-$G_{t-2}$ in a second interval (t−2 to t−1) fall in a range of 0 to +10, bio-information transition from $G_{t-1}$ to $G_t$ in an interval from t−1 to a current time point t is most likely to fall in a range of 0 to +10. Therefore, the corrector 213 may correct a missing value $N_t$ by adding a constant k to a bio-information value $G_{t-1}$ of the preceding time point t−1, as shown in Equation 4 below. Here, k may be an arbitrary number (e.g., an intermediate value of 5) which allows transition from the preceding time point t−1 to the current time point t to have a range of 0 to +10.

$$G_t = G_{t-1} + k \quad (4)$$

Figure 6C:
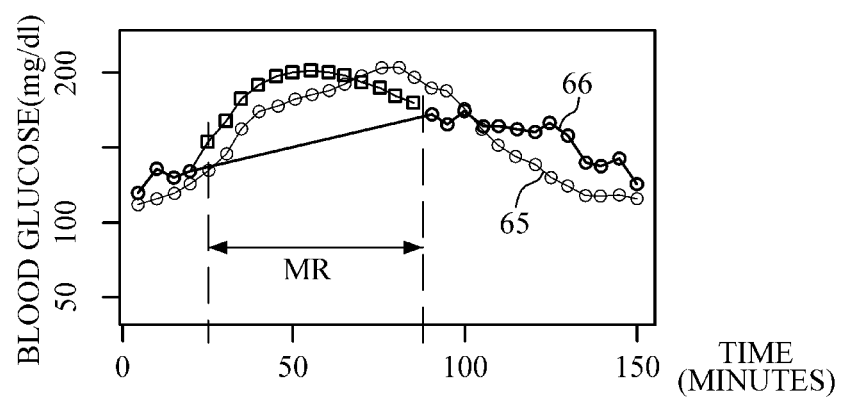

FIG. 6C shows a blood glucose measurement result 66 when the user does not wear the bio-information sensor 110 or the bio-information is not measured for a considerable amount of time, e.g., due to power off of the bio-information sensor 110. In this case, an interval MR from about 25 minutes to about 80 minutes represents a missing interval where a measurement is not actually performed. The corrector 213 may estimate the missing interval as a missing value and correct (e.g., replace) the missing value. Values of points indicated by circles in the blood glucose measurement result 66 in FIG. 6C indicate bio-information measurements or corrected values obtained by correcting biometric information measurements, and values at points indicated by rectangles indicate corrected values for missing values. It can be seen that the whole blood glucose measurement result 66 after the correction of the missing values becomes very similar to blood glucose levels 65 that are actually measured through blood collection.

Figure 6D:
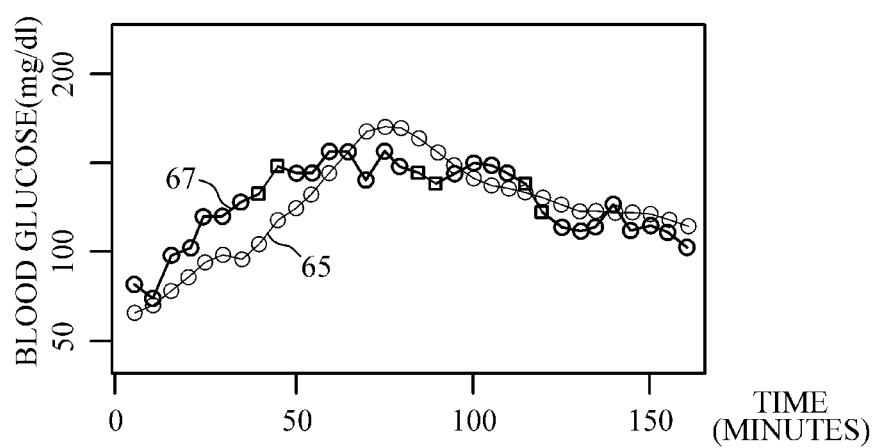

FIG. 6D shows an example in which momentary missing values occur due to a poor contact between the bio-information sensor 110 and the part to be inspected even when the user is wearing the bio-information sensor 110. Similarly to FIG. 6C, values of points indicated by circles in a blood glucose measurement result 67 in FIG. 6D indicate the bio-information measurements or corrected values obtained by correcting the measurements, and values of points indicated by rectangles indicate corrected values obtained by correcting missing values.

Referring back to FIG. 2, the outputter 240 may provide a processing result of the processor 210 to the user. For example, the outputter 240 may visually output a current bio-information correction result as a final bio-information value to the display, or may output it in an audible manner, such as voice. In addition, the continuous bio-information measurements received from the bio-information sensor 110 or a result of correcting the continuous measurements may be output in the form of a graph. However, exemplary embodiments are not limited thereto, and the outputter 240 may be variously embodied in accordance with output methods. For example, the outputter 240 may output an audio signal and/or a video signal and may include the display and/or an audio output device, e.g., a speaker, audio jack, audio output device, etc.).

A variety of reference information to be used for bio-information measurement and correction may be stored in the storage 250. For example, the reference information may include user information, such as the age, sex and health status of the user, and information about the aforementioned physiological metabolic model, a bio-information database, a bio-information correction formula, and a correlation model. In addition, the food intake information and the metabolic information acquired by the processor 210 and the continuous bio-information measurements and the bio-information correction result received from the bio-information sensor 110 may be stored. The storage 250 may include, but not limited to, one or more types of storage media including a flash memory, a hard disk, a multimedia card micro type memory, a card-type memory (e.g., secure digital (SD) or eXtreme digital (XD) memory, etc.) a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, According to exemplary embodiments, when the bio-information is measured by a bio-information sensor in a non-invasive manner, it is possible to accurately measure the bio-information by correcting the bio-information measurements, the outlier values and the missing values using the user's metabolic information. Therefore, the solutions according to exemplary embodiments solve the problems in that conventional non-invasive methods of estimating a biological component are not accurate as invasive methods and require monitoring and/or removal of a noise.

Figure 7:
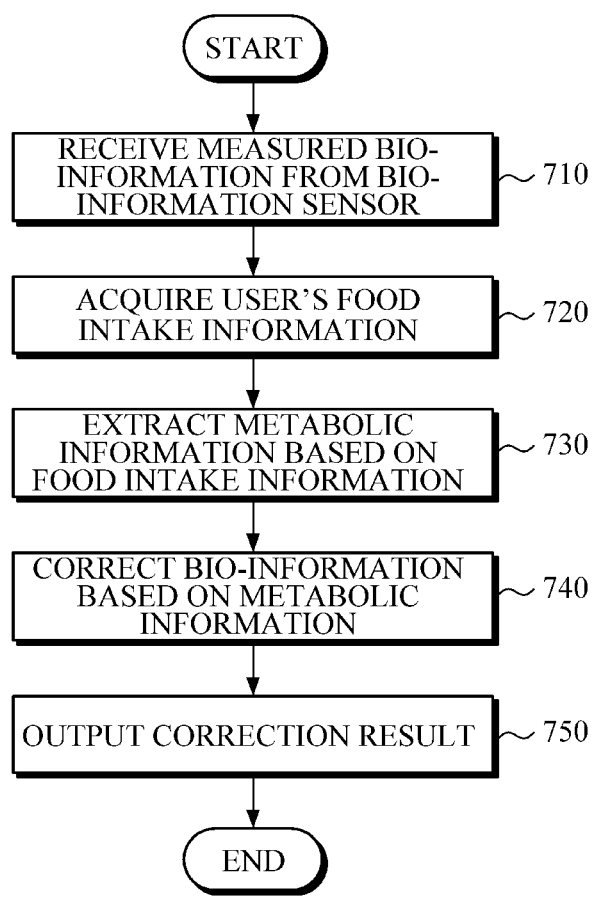
FIG. 7 is a flowchart illustrating a method of correcting an error of a bio-information sensor according to an exemplary embodiment.

FIG. 7 is a flowchart illustrating a method of correcting an error of a bio-information sensor according to an exemplary embodiment.

The method shown in FIG. 7 is an exemplary embodiment of an error correction method performed by the error correction apparatus of the bio-information sensor in accordance with an exemplary embodiment of FIG. 2. Various exemplary embodiments of the error correction method performed by the error correction apparatus 200 have been described, and thus will be described in brief hereafter.

The error correction apparatus 200 receives bio-information measured by the bio-information sensor in operation 710. In this case, the bio-information sensor may be a continuous measurement sensor that measures the user's bio-information continuously.

The error correction apparatus 200 acquires the user's food intake information in operation 720. In this case, the food intake information may include a type and an amount of food eaten, the time of food intake, and the like. For example, the error correction apparatus 200 may acquire food intake sensor information about the user's food intake from the food intake sensor, and acquire the food intake information based on the acquired food intake sensor information. In another example, the error correction apparatus 200 may obtain a slope change of the bio-information by analyzing the continuous bio-information measurements received in operation 710 and determine that a time at which the slope change is abrupt is when the user takes food. In another example, the user may input food intake information, such as a type and an amount of food taken by the user, the food intake time, and the like, through an interface.

The error correction apparatus 200 extracts metabolic information related to the bio-information based on the food intake information in operation 730. In this case, the metabolic information may include a change amount of bio-information with respect to time, a confidence interval of the bio-information, and probability information of each variation range of the bio-information. The error correction apparatus 200 may extract a change amount of bio-information according to the user's food intake using a physiological metabolic model personalized to each user. Alternatively, the error correction apparatus 200 may extract a change amount and a confidence interval of the bio-information, probability information of each variation range of the bio-information, and the like by using a bio-information database.

The error correction apparatus 200 corrects the bio-information measured by the bio-information sensor based on the extracted metabolic information in operation 740. For example, the error correction apparatus 200 may correct continuous bio-information measurements measured based on the change amount of the bio-information. In addition, the error correction apparatus 200 may determine an outlier value among the continuous bio-information measurements based on the confidence interval of the bio-information, and replace the determined outlier value with a value in the confidence interval. Further, the error correction apparatus 200 may estimate a missing value by analyzing the continuous bio-information measurements and correct the estimated value based on the probability information of each variation range of the bio-information.

The error correction apparatus 200 outputs a result of correcting the bio-information in operation 750. At this time, the error correction apparatus may visually output the bio-information correction result by displaying the bio-information correction result to a display, or may convert the bio-information correct result into a voice signal and audibly output the voice signal to the user through a speaker module.

Figure 8:
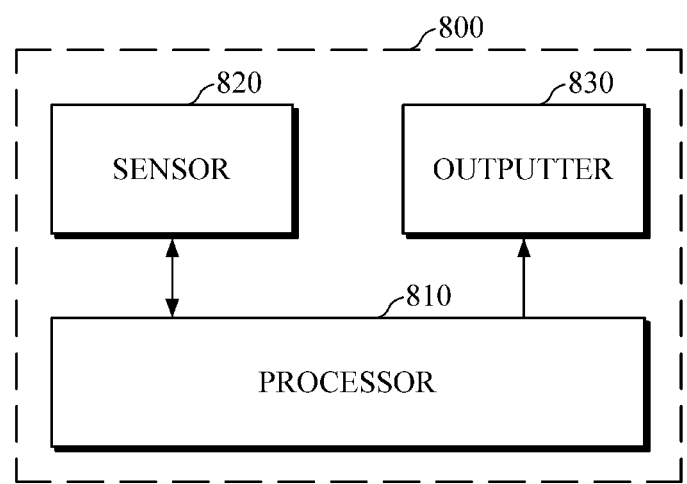
FIG. 8 is a block diagram illustrating an apparatus for estimating bio-information according to an exemplary embodiment.

FIG. 8 is a block diagram illustrating an apparatus 800 for estimating bio-information according to an exemplary embodiment.

Figure 9:
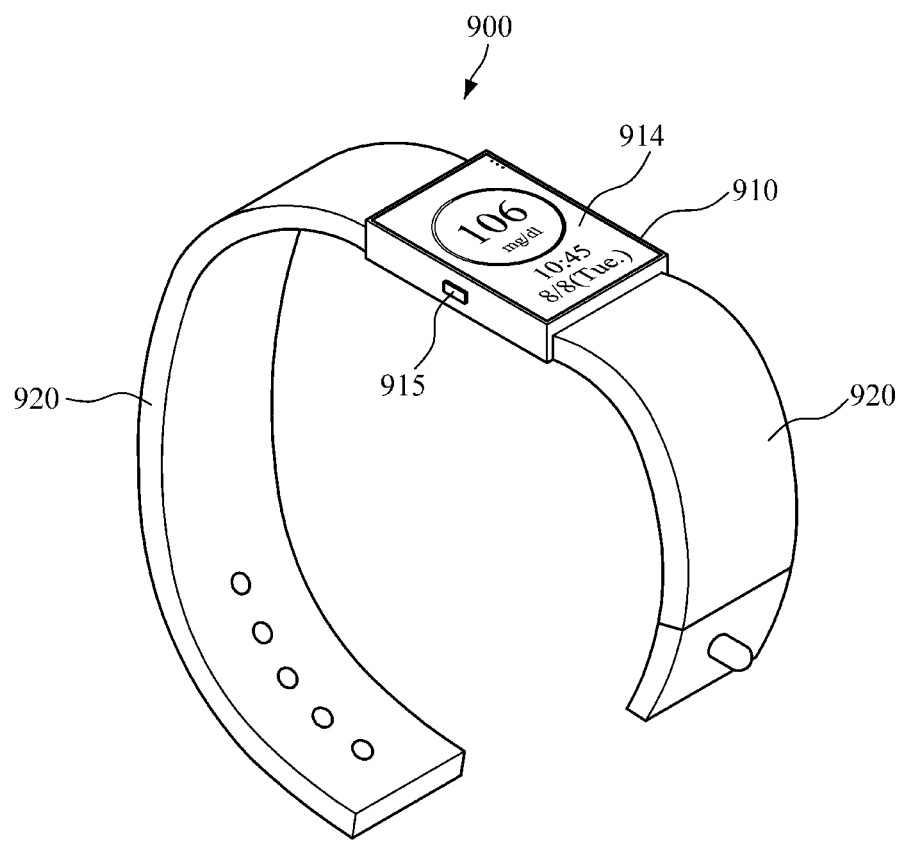
FIG. 9 is a diagram illustrating a wearable device according to an exemplary embodiment.

The apparatus 800 for estimating bio-information according to an exemplary embodiment may be an apparatus that non-invasively estimates a variety of bio-information including blood glucose, cholesterol, triglycerides, protein, alcohol, and uric acid. According to an exemplary embodiment, the apparatus 800 may be implemented as a wristwatch-type wearable device, as shown in FIG. 9. However, exemplary embodiments are not limited thereto, and the wearable device may be of any other types, for example, a bracelet-type, a wristband type, a ring type, a glasses type, a hairband type, or the like and may be provided in various sizes and forms depending on the purpose of bio-information estimation or the place where the bio-information estimation apparatus is used. Alternatively, the apparatus 800 may be mounted in an information processing device, such as a smartphone, a tablet PC, or the like.

Referring to FIG. 8, the apparatus 800 includes a processor 810, a sensor 820, and an outputter 830.

The sensor 820 may collect sensor information from a user under the control of the processor 810. For example, the sensor 810 may include a non-invasive sensor, such as a spectroscopic sensor, an impedance sensor, an ultrasonic sensor, a thermal sensor, an ECG sensor, an EEG sensor, an EMG sensor, an EOG sensor, or a PPG sensor, and collect sensor information, such as spectral information, impedance measurement information, ultrasound measurement information, thermal measurement information, ECG information, EEG information, EMG information, EOG information, or PPG information. Hereinafter, for convenience of description, a case in which the sensor 820 includes a spectroscopic sensor and spectral information is acquired through the spectroscopic sensor as sensor information will be taken as an example.

The spectroscopic sensor may include a light source configured to emit light onto a body part of the user to be inspected and a detector configured to detect light scattered or reflected back from the irradiated body part after the emitted light has been absorbed by the tissue of the body part. In this case, the light source may be a light emitting diode (LED), a laser diode, a phosphor, and the like. The light source may be configured to emit near infrared light, but is not limited thereto, and may emit a single laser beam. In addition, the detector may include a photodiode.

In addition, the sensor 820 may include a food intake sensor configured to collect food intake sensor information by detecting the user's food intake. The food intake sensor may be a sensor configured to recognize the sound of food intake or swallowing, or a muscle movement of the user, or capture an image of food that the user is eating. The food intake sensor may be mounted in one body structure along with the other configurations, such as the spectroscopic sensor, the processor 810, and the outputter 830, but is not limited thereto. For example, the food intake sensor may be implemented as a separate device to be worn on a body part (e.g., an ear, a wrist, etc.) of the user, and transmit food intake sensor information to the processor 810 via a wired and/or wireless communication through a communication module mounted in the apparatus 800.

The processor 810 may control the sensor 820 when the processor 810 receives a request for estimating bio-information, and may receive sensor information from the sensor 820. The processor 810 may estimate bio-information by using the sensor information received from the sensor 810 and provide an estimation result to the user through the outputter 830. For example, the processor 810 may include a central processing unit (CPU).

When the processor 810 receives the request for estimating bio-information from the user or an external device, the processor 810 may drive the light source to emit light to the body part of the user to be inspected by controlling the spectroscopic sensor. In addition, when spectrum information is received from the detector, the processor 810 may estimate bio-information by applying a bio-information estimation model. In this case, the bio-information estimation model may be a linear function that represents a correlation between a spectrum and the bio-information.

The processor 810 may acquire food intake information related to the bio-information when the user has eaten food. In this case, the food intake information may include a type or an amount of food that the user has eaten, time of food intake, and the like. In one example, when the food intake sensor information is received from the food intake sensor, the food intake information may be acquired by analyzing the received food intake sensor information. In another example, the processor 810 may provide a user interface to the user through the outputter 830 and receive food intake information input by the user through the interface. In still another example, the processor 810 may monitor continuous bio-information estimates, and determine that a time interval in which a slope change of the continuous bio-information estimates that is monitored is greater than a threshold range is the time when the user takes food. In addition, a type or an amount of food that has been eaten may be estimated according to the bio-information estimates and a slope change of the bio-information estimates by referring to a bio-information database personalized to each user. However, exemplary embodiments are not limited to the above examples. For example, the food intake information may be acquired by combining results of the above two or more examples or using other pieces of information which have not been illustrated.

When the user's food intake information is acquired, the processor 810 may extract metabolic information using the acquired food intake information. The metabolic information may include a change amount over time of bio-information, a confidence interval, probability information of each variation range, or the like. For example, as described above, the processor 810 may extract the metabolic information using a physiological metabolic model or a bio-information database which is provided in advance and personalized to the user according to the type and amount of food that the user has eaten, and the time of food intake.

When the metabolic information is extracted, the processor 810 may correct bio-information estimated based on one or more of a bio-information estimation formula according to an exemplary embodiment. For example, a bio-information estimate and a bio-information variation at the same point in time may be input to a predefined bio-information correction formula to output corrected bio-information. In this case, examples of the bio-information correction formula are illustrated in Equation 1 or Equation 2.

In another example, the processor 810 may extract an outlier value that is out of the confidence interval of the bio-information from among the bio-information estimates based on confidence interval information of the bio-information, and may replace the extracted outlier value with a value within the confidence interval. For example, the processor 810 may replace the outlier value with a boundary value of the confidence interval (e.g., a value equal to or less than a maximum value of the confidence interval or a value equal to or greater than a minimum value of the confidence interval) at the same point in time. Alternatively, the processor 810 may correct the outlier value of a certain time point using an average or intermediate value of normal values (e.g., normal estimates of the bio-information or corrected values of outlier values or corrected values of missing values) of a preceding and a subsequent time points, or an average or intermediate value of weighted normal values of a preceding and a subsequent time points, but the values to be used in correction are not particularly limited to the these examples.

In another example, the processor 810 may estimate a missing value by analyzing the bio-information estimates and correct the missing value using the metabolic information. For example, as described with reference to Equation 3 or Table 1 above, the processor 810 may correct the missing value using a variation of bio-information or probability information of each variation range.

When the estimation and correction of the bio-information is completed, the processor 810 may perform various actions based on the correction result. For example, the processor 810 may transmit the correction result to an external device that has requested the bio-information estimation. In addition, the processor 810 may generate a graph showing a comparison between the bio-information estimation result and the correction result. Further, the processor 810 may monitor a health status of the user based on the bio-information correction result to determine whether the health status is normal, and generate alarm or warning information to be provided to the user.

The processor 810 may compare the bio-information estimation result and the correction result to determine whether to calibrate the bio-information estimation model. For example, the processor 810 may obtain a difference between the bio-information estimate and the corrected value at each point in time and when the number of occurrences that the difference exceeds a threshold meets a predetermined criterion, the processor 810 may determine to calibrate the bio-information estimation model.

When the processor 810 determines to calibrate the bio-information estimation model, the processor 810 may receive a bio-information measurement from an external device, for example, a non-invasive bio-information measurement apparatus and calibrate the bio-information estimation model.

The outputter 830 may provide a processing result of the processor 810 to the user. For example, the outputter 830 may display the bio-information correction result on a display as final bio-information or output the result in a sound and/or voice form. In addition, the outputter 830 may display warning and/or alarm information and a graph showing a comparison result of the bio-information estimate and the corrected value on the display. Further, the outputter 830 may provide the warning and/or alarm information by generating vibration or tactile sensation. To this end, the outputter 830 may include a display, an audio output device (e.g., speaker, audio jack, audio output device), and/or a haptic module (e.g., vibration motor). However, exemplary embodiments are not limited to these examples and the outputter 830 may be variously embodied in accordance with output methods.

FIG. 9 is a diagram illustrating a wearable device according to an exemplary embodiment. FIG. 9 shows a wearable device in the form of a smart watch that is worn on the user's wrist and implements the bio-information estimating apparatus of FIG. 8.

Referring to FIG. 9, the wearable device 900 includes a main body 910 and a strap 920. The processor 810, the sensor 820, and the outputter 830 of the bio-information estimating apparatus 800 shown in FIG. 8 may be mounted inside the main body 910 or be mounted in such a manner that they are exposed to the outside.

The main body 910 may be worn on a user's wrist by the strap 920, and the strap 920 may be connected to a first side and a second side of the main body 910 to be fastened to each other. The strap 920 may include a flexible member to wrap around the wrist.

A battery may be equipped in the main body 910 and/or the strap 920 to supply power to the wearable device.

The wearable device 900 may include a spectroscopic sensor mounted in the main body 910 and configured to measure a spectrum of the user's wrist part. The spectroscopic sensor may include a light source and a detector. The light source may be mounted on a lower part of the main body 910 and be exposed to the wrist so as to emit light to the wrist part of the user. The detector may include a photodiode and detect light returning from the user's skin to acquire a spectrum. However, the sensor to be mounted in the wearable device 900 is not limited to the spectroscopic sensor, as described above, and one or more various non-invasive sensors may be mounted in the main body 910 depending on embodiments.

The wearable device 900 may include a gyro sensor configured to acquire inclination information of the main body 910 and a camera module (e.g., camera) configured to collect image information related to a type of food that the user is taking. In addition, the wearable device 900 may include a communication module for communicating with the food intake sensor configured to acquire information about a food intake sound, recognition of neck swallowing and neck muscle movement, etc. while the user is taking food.

The processor 810 mounted inside the main body 910 may receive a user's instruction input through an operator 915 and/or a display 914 and perform an operation in response to the received instruction. For example, the processor 810 may electrically connected to the spectroscopic sensor, generate a control signal for controlling the spectroscopic sensor when receiving a bio-information estimation instruction from the user, and transmit the control signal to the spectroscopic sensor. When the spectroscopic sensor acquires spectral information, the processor 810 may receive the spectral information and estimate bio-information by using a bio-information estimation model.

In addition, when the user takes food, the processor 810 may receive sensor information related to user's food intake from the gyro sensor, the camera module, and the food intake sensor, and acquire the user's food intake information by analyzing the received sensor information. In addition, as described above, the processor 810 may analyze the bio-information measurements to acquire food intake information or directly receive the food intake information from the user.

The processor 810 may communicate with an external device by controlling the communication module. The processor 810 may transmit the bio-information estimates and/or corrected values to the external device so that the external device can perform various functions related to monitoring of a user's health status. The external device may be an information processing device, such as a smartphone, a tablet PC, a desktop PC, a notebook PC, which has a relatively excellent computing performance.

The wearable device 900 may further include the display 914 mounted on an upper part of the main body 910 and configured to provide a processing result of the processor 810 to the user. For example, the display 914 may output the corrected value of the bio-information as final bio-information. In addition, the display 914 may display a result of comparison between the bio-information estimate and a corrected value of the bio-information, warning and alarm information, and the like. Moreover, the display 914 may display an interface through which various instructions are received from or guided to the user, and may transmit information input through the interface to the processor 810. The display 914 may be formed as a module capable of touch input.

The wearable device 900 may further include the operator 915 mounted in the main body 910. The operator 915 may be formed on one side of the main body 910 to be exposed to the outside, receive the instruction input by the user, and transmit the instruction to the processor 810. The operator 915 may include a function of turning on/off the power of the wearable device.

Figure 10:
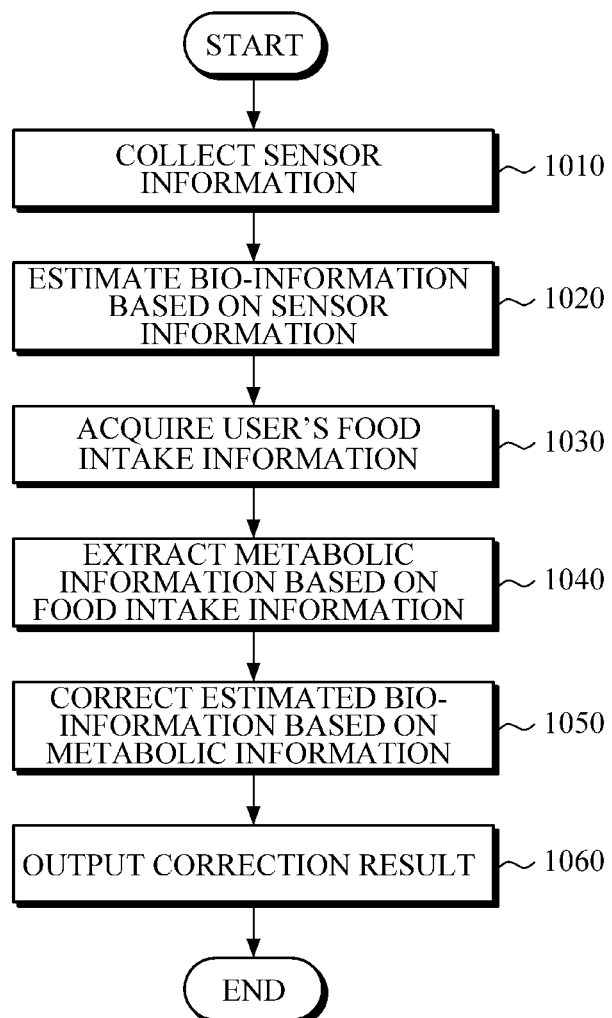
FIG. 10 is a flowchart illustrating a method of estimating bio-information according to an exemplary embodiment.

FIG. 10 is a flowchart illustrating a method of estimating bio-information according to an exemplary embodiment.

The method shown in FIG. 10 may be performed by the apparatus 800 for estimating bio-information illustrated in FIG. 8. Various exemplary embodiments of the method of estimating bio-information has been described above, and thus a brief description thereof will be given below.

The apparatus 800 for estimating bio-information collects sensor information from a user in operation 1010. For example, spectral information may be acquired from the user through a spectroscopic sensor. In this case, the spectroscopic sensor may continuously acquire the spectral information at predetermined time intervals. In addition, when the user takes food, food intake sensor information may be collected through a food intake sensor that recognizes the user's food intake.

The apparatus 800 estimates bio-information based on the sensor information in operation 1020. The apparatus 800 may estimate the bio-information based on the spectral information acquired by the spectroscopic sensor and, at this time, may estimate the bio-information using a bio-information estimation model provided in advance.

In operation 1030, the apparatus 800 acquires the user's food intake information using at least one of the food intake sensor information collected by the food intake sensor in operation 1010, the continuous bio-information estimates obtained in operation 1020, and the food intake information input by the user.

In operation 1040, when the user's food intake information is acquired, the apparatus 800 extracts metabolic information by referring to a physiological metabolic model or a bio-information database. In this case, the physiological metabolic model and the bio-information database may be personalized to each user and provided in advance, and may include information indicating a correlation between the food intake information, such as the type and amount of food taken by the user, the food intake time, and the like, and the change in bio-information over time.

In operation 1050, the apparatus 800 corrects the bio-information estimated in operation 1020 using the extracted metabolic information. For example, the apparatus 800 may correct the bio-information estimates obtained in operation 1020 based on a change amount over time of the bio-information. In addition, an outlier value is extracted from the bio-information estimates based on the confidence interval information with respect to time, and the extracted outlier value may be corrected. In addition, a missing value in an interval or at a point in time at which a bio-information estimate is missing is estimated and the estimated missing value is corrected based on a change amount over time of the bio-information or the probability information of each variation range.

In operation 1060, the apparatus 800 outputs the bio-information correction result obtained in operation 1050. In addition, the apparatus 800 may output a result of comparison between the bio-information estimate and the corrected value or warning/alarm information. In this case, the apparatus 800 may visually output the information by varying color, font size, or thickness, or may output the information using a non-visual means, such as a voice, tactile sensation, vibration, or the like, or output the information using both a non-visual means and a visual means at the same time.

The exemplary embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

According to exemplary embodiments, when the bio-information is measured by a bio-information sensor, it is possible to accurately measure the bio-information by correcting the bio-information measurements, the outlier values and the missing values using the user's metabolic information.

At least one of the components, elements or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, processing, logic, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating bio-information, comprising:
   a sensor configured to obtain sensor information from a user; and
   a processor configured to estimate the bio-information based on the sensor information, extract metabolic information based on food intake information of the user, correct the estimated bio-information using the extracted metabolic information, and provide a result of correcting the estimated bio-information,
   wherein the processor is further configured to determine at least one of an outlier value in the estimated bio-information which is out of a confidence interval or a missing value in the estimated bio-information at a point in time in which the sensor information is not obtained from the user, correct the at least one of the outlier value or the missing value using the extracted metabolic information, and provide a result of correcting the at least one of the outlier value or the missing value.

2. The apparatus of claim 1, wherein the sensor information comprises at least one from among spectrometer measurement information, impedance measurement information, ultrasonic measurement information, thermal measurement information, electrocardiography (ECG) information, electroencephalogram (EEG) information, electromyography (EMG) information, electrooculography (EOG) information, and photoplethysmography (PPG) information.

3. The apparatus of claim 1, wherein the sensor comprises a food intake sensor configured to acquire food intake sensor information by detecting a food intake of the user, and the processor is further configured to acquire the food intake information based on the food intake sensor information.

4. The apparatus of claim 1, wherein the processor is further configured to extract the metabolic information by using at least one from among a physiological metabolic model and a bio-information database.

5. The apparatus of claim 1, wherein the metabolic information comprises at least one from among a change amount of the bio-information over time, the confidence interval of the bio-information, and a probability of the change amount being in a certain variation range.

6. The apparatus of claim 5, wherein the processor is further configured to correct an estimate of the bio-information by using at least one from among a correlation model and a correction formula indicating a correlation between the estimate of the bio-information and the change amount of the bio-information over time or the probability of the change amount being in the certain variation range.

7. The apparatus of claim 5, wherein the processor is further configured to correct an outlier value among estimates of the bio-information which is out of the confidence interval to be a value within the confidence interval.

8. The apparatus of claim 5, wherein the processor is further configured to correct the missing value based on at least one from among the change amount of the bio-information over time and the probability of the change amount of the bio-information being in the certain variation range.

9. A method of estimating bio-information, comprising:
   obtaining sensor information from a user;
   estimating bio-information based on the sensor information;
   acquiring food intake information of the user;
   extracting metabolic information based on the food intake information; and
   correcting the estimated bio-information based on the extracted metabolic information and providing a result of correcting the estimated bio-information,
   wherein the correcting comprises:
      determining at least one of an outlier value in the estimated bio-information which is out of a confidence interval or a missing value in the estimated bio-information at a point in time in which the sensor information is not obtained from the user; and
      correcting the at least one of the outlier value or the missing value using the extracted metabolic information, and
   wherein the providing the result comprises providing a result of correcting the at least one of the outlier value or the missing value.

10. The method of claim 9, wherein the sensor information comprises at least one from among spectrometer measurement information, impedance measurement information, ultrasonic measurement information, thermal measurement information, ECG information, EEG information, EMG information, EOG information, and PPG information.

11. The method of claim 9, wherein the obtaining the sensor information comprises obtaining food intake sensor information by using a food intake sensor configured to detect a food intake of the user and the acquiring the food intake information comprises acquiring the food intake information of the user based on the food intake sensor information.

12. The method of claim 9, wherein the extracting the metabolic information comprises extracting the metabolic information by using at least one from among a physiological metabolic model and a bio-information database.

13. The method of claim 9, wherein the correcting the bio-information comprises correcting the outlier value which is out of the confidence interval of the bio-information to be a value within the confidence interval.

14. The method of claim 9, wherein the correcting the bio-information comprises correcting the missing value based on at least one from among a change amount of the bio-information over time and a probability of the change amount of the bio-information being in a certain variation range.

* * * * *